United States Patent [19]

Chu et al.

[11] Patent Number: 5,157,185
[45] Date of Patent: Oct. 20, 1992

[54] ALKYLATION OF AROMATICS

[75] Inventors: Yung F. Chu, Plainsboro; David O. Marler, Deptford; John P. McWilliams, Woodbury, all of N.J.

[73] Assignee: Mobil Oil Corporation, Fairfax, Va.

[21] Appl. No.: 402,018

[22] Filed: Sep. 1, 1989

[51] Int. Cl.$^5$ ............................................. C07C 2/66
[52] U.S. Cl. ..................................... 585/467; 502/71; 502/77
[58] Field of Search ...................... 585/467; 502/77, 71

[56] References Cited

U.S. PATENT DOCUMENTS

| Re. 27,639 | 5/1973 | Thomas et al. | 260/672 T |
|---|---|---|---|
| 2,904,607 | 9/1959 | Mattox et al. | 260/671 |
| 3,251,897 | 5/1966 | Wise | 260/671 |
| 3,551,509 | 12/1970 | Thomas et al. | 260/672 |
| 3,641,177 | 2/1972 | Eberly et al. | 585/467 |
| 3,751,504 | 8/1973 | Keown et al. | 260/672 T |
| 3,751,506 | 8/1973 | Burress | 260/671 R |
| 3,962,364 | 6/1976 | Young | 260/671 C |
| 3,965,209 | 6/1976 | Butter et al. | 585/467 |
| 4,016,218 | 4/1977 | Haag et al. | 260/671 R |
| 4,094,921 | 6/1978 | Kaeding et al. | 585/467 |
| 4,117,024 | 9/1978 | Kaeding | 585/467 |
| 4,127,616 | 11/1978 | Rodewald | 260/671 R |
| 4,128,592 | 12/1978 | Kaeding | 585/467 |
| 4,169,111 | 9/1979 | Wight | 585/323 |
| 4,324,940 | 4/1982 | Dessau | 585/467 |
| 4,326,994 | 4/1982 | Haag et al. | 502/77 |
| 4,361,713 | 11/1982 | Kaeding | 585/467 |
| 4,365,104 | 12/1982 | Kaeding | 585/467 |
| 4,367,359 | 1/1983 | Kaeding | 585/467 |
| 4,370,508 | 1/1983 | Kaeding | 585/467 |
| 4,380,685 | 4/1983 | Chu | 585/466 |
| 4,384,155 | 5/1983 | Chu | 585/466 |
| 4,418,235 | 11/1983 | Haag et al. | 585/470 |
| 4,420,418 | 12/1983 | Chu | 502/77 |
| 4,547,605 | 10/1985 | Kresge et al. | 585/467 |
| 4,548,914 | 10/1985 | Chu | 502/77 |
| 4,599,475 | 10/1985 | Kresge et al. | 585/481 |
| 4,626,609 | 12/1986 | Shihabi | 585/467 |
| 4,694,114 | 9/1987 | Chu et al. | 585/481 |

FOREIGN PATENT DOCUMENTS 0141514 5/1985 European Pat. Off. .

Primary Examiner—Anthony McFarlane
Attorney, Agent, or Firm—Alexander J. McKillop; Charles J. Speciale; Laurence P. Hobbes

[57] ABSTRACT

Alkylation of aromatics, e.g. ethylbenzene preparation, with minimized o-xylene make by contacting with olefin alkylating agent in the presence of ZSM-5 crystals having a diffusion rate constant of at least about 100 sec$^{-1} \times 10^{-6}$ and an alpha value of less than about 100 prepared from a non-organic forming mixture comprising a silica source of precipitated silica having a particle size of 1 to 500 microns.

23 Claims, 1 Drawing Sheet

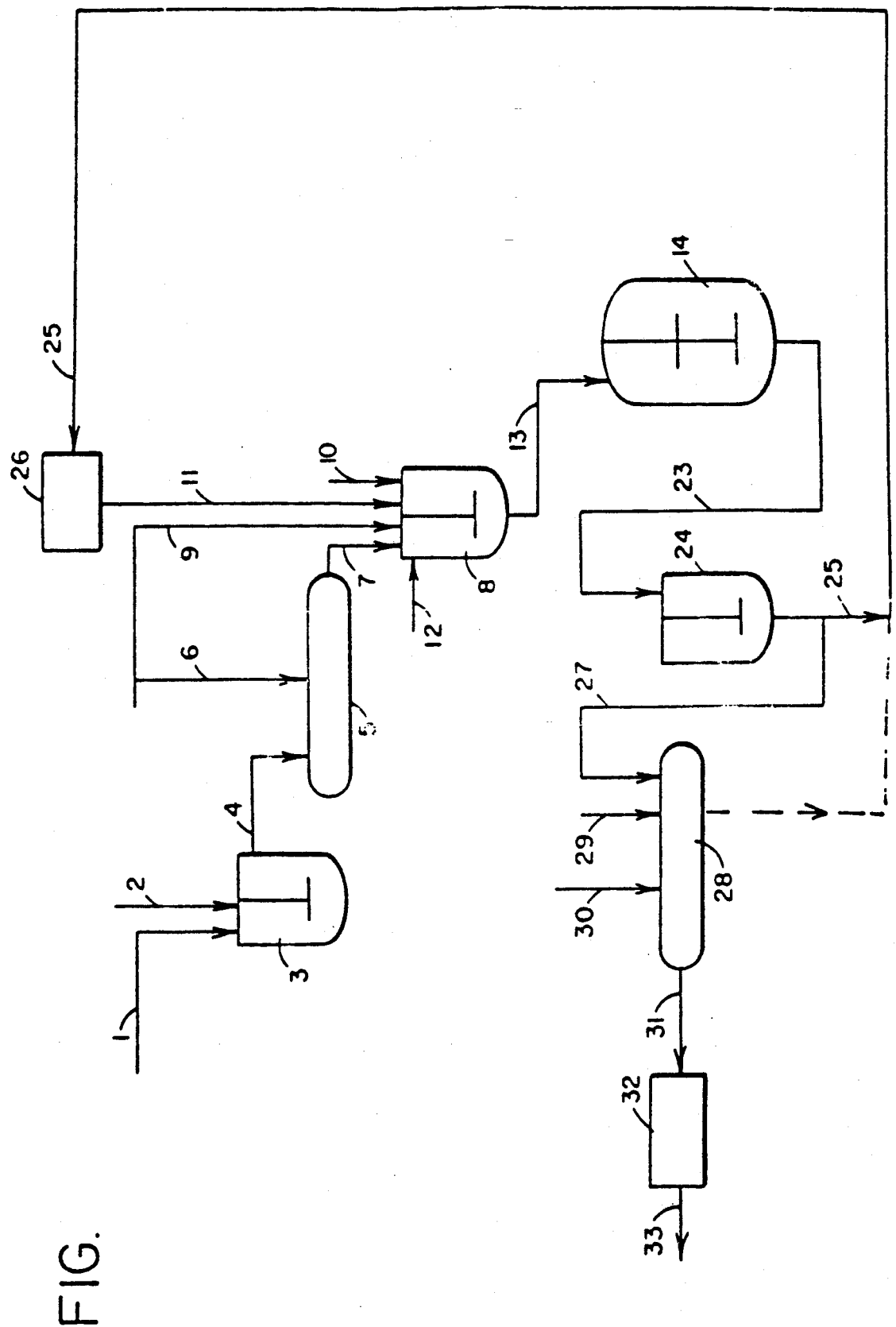
FIG.

ALKYLATION OF AROMATICS

This application is filed under 35 U.S.C. 120, based on Ser. No. 092,504, filed Sep. 2, 1987, which is relied upon and incorporated by reference herein.

This invention relates to a process for the alkylation of an aromatic hydrocarbon by reaction with an olefin in the presence of a porous crystalline silicate ZSM-5 catalyst which has an alpha value below about 100 and a diffusion rate constant $(D/r^2)$ of at least about 100 $sec^{-1} \times 10^{-6}$.

Alkylation of aromatic hydrocarbons utilizing porous crystalline silicate catalysts has heretofore been described. U.S. Pat. No. 2,904,607 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes liquid phase alkylation in the presence of X- or Y-type crystalline aluminosilicate zeolite, specifically such type zeolites wherein the cation is rare earth and/or hydrogen. U.S. Pat. No. 3,751,504 to Keown et al., and U.S. Pat. No. 3,751,506 to Burress describe vapor phase alkylation of aromatic hydrocarbons with olefins, e.g., benzene with ethylene in the presence of a ZSM-5 zeolite catalyst. U.S. Pat. No. 4,016,218 to Wise describes vapor phase alkylation with a shape-selective zeolite such as ZSM-5 which has been modified by steaming to an alpha value less than 250. All of the above patents are incorporated herein by reference.

While the latter type catalysts represent a distinct improvement over previously suggested crystalline aluminosilicate catalysts particularly with respect to improved aging properties, they have the disadvantage of producing unwanted quantities of impurities along with the desired alkyl aromatic product, thereby decreasing the overall yield and selectivity for such product.

Thus, in the alkylation of benzene with ethylene, while desired ethylbenzene is the major product, small amounts of di- and possibly triethylbenzenes are always produced simultaneously with ethylbenzene, such amounts depending on the conversion of benzene to ethylbenzene. The polyethylbenzenes formed can be recycled to the alkylation zone, where they undergo transalkylation with benzene to produce more ethylbenzene. Alternatively, the polyethylbenzenes can be transalkylated with benzene in a separate reactor. The formation of polyethylbenzenes hence does not constitute an ultimate loss of the alkylating agent, ethylene. On the other hand, aromatic compounds other than ethylbenzene and polyethylbenzenes, that are formed during the alkylation reaction, generally referred to as by-products, result in an irreversible loss of ethylene and cause difficulties in the product purification. By-products produced during ethylation of benzene include, for example, toluene, xylenes, cumene, n-propylbenzene, ethyltoluene, butylbenzene and other $C_{10}+$ aromatics, the majority being $C_7$-$C_9$ aromatics. Production of o-xylene is especially undesirable in view of its relatively low commercial value. The formation of these by-products is increased when the benzene conversion to ethylbenzene is high. Due to the high exothermicity of the alkylation reaction, ethylbenzene synthesis is generally carried out in a multiplicity of reactors with interstage cooling and addition of ethylene to the various stages, the ethylbenzene concentration increasing in subsequent stages. Undesired by-products are accordingly formed in increasing amounts in the latter stages of the process.

U.S. application Ser. No. 092,503 filed Sep. 2, 1987, filed contemporaneously with the present application relates to a method for transalkylating an aromatic hydrocarbon charge utilizing a catalyst similar to but of higher activity than the catalyst employed in the present invention.

U.S. application Ser. No. 092,842, filed Sep. 2, 1987, filed contemporaneously with the present application, relates to a vapor phase disproportionation of toluene, utilizing catalysts similar to those employed in the present invention.

U.S. application Ser. No. 014,147, filed Feb. 12, 1987 relates to a method for preparing zeolites from a non-organic reaction mixture having a low silica to alumina molar ratio such as those used in the present invention.

U.S. application Ser. No. 092,505, filed Sep. 2, 1987, filed contemporaneously with the present application, relates to a method for preparing small crystal zeolites having a low silica to alumina molar ratio from a non-organic reaction mixture such as those used in the present invention.

In accordance with the present invention, there has been discovered a process for decreasing the selectivity for o-xylene while using a catalyst which affords a high yield of the alkylate of interest over a long and commercially attractive period of time.

The process comprises effecting alkylation of aromatic hydrocarbons by contacting the same with an olefin under conditions effective for accomplishing said alkylation, e.g., a reactor inlet temperature between about 575° F. and 900° F., preferably with a reactor bed temperature as much as 250° F. above the reactor inlet temperature, a pressure between atmospheric and about 3000 psig, employing a mole ratio of hydrocarbon charge aromatic to olefin alkylating agent in the approximate range of 1:1 to 30:1 and a total feed weight hourly space velocity between about 2 and about 2000, in the presence of a catalyst having an alpha value below about 100 preferably below about 75, say from about 30 to 65, comprising a porous crystalline silicate having the structure of ZSM-5 and having a diffusion rate constant $(D/r^2)$ of at least about 100 $sec^{-1} \times 10^{-6}$, preferably at least about 150, say greater than from about 175 $sec^{-1} \times 10^{-6}$ where D=the diffusion coefficient ($cm^2$/sec) and r=the crystal radius (cm).

Diffusivities are determined by measuring the time $(t_{0.3})$ it takes to sorb 30% of o-xylene (of total o-xylene capacity) by the rate constant determination test described in U.S. Pat. No. 4,117,026, incorporated herein by reference as to that description. The characteristic diffusion time, $t_{0.3}$, is a direct measure of the critical mass transfer property $r^2/D$.

The porous crystalline silicates used in the present process can be prepared from a non-gelling, non-organic forming mixture having a solids content of at least about 30, preferably at least about 35 weight percent comprising a silica source of precipitated silica having a particle size of 1 to 500 microns, a source of alkali metal and a source of water.

Methods for preparing such materials are disclosed in U.S. application Ser. No. 014,147 and U.S. application Ser. No. 092,505 noted above. These processes allow for flexibility in the exact composition of the zeolite product. That is, by controlling the exact components which constitute the crystallization reaction mixture from which the zeolite is crystallized, control of the product composition is possible. In preparing zeolites by this process, an essential component of the zeolite crystallization reaction mixture is a silica precipitate, the particle size of which is in the range of 1 to 500 microns. Moreover, the silica precursor precipitation can be undertaken in a liquid reaction mixture to which no aluminum or alumina source has been added; this embodiment provides great flexibility in varying the Si:Al atomic ratio (or $SiO_2/Al_2O_3$ molar ratio) in the zeolite composition. It is noted that the zeolites used in the present application have a $SiO_2/Al_2O_3$ of less than 100 and preferably molar ratios of less than about 40.

ZSM-5 is described in U.S. Pat. No. 3,702,886. That description, and in particular the X-ray diffraction pattern of said ZSM-5, is incorporated herein by reference.

It is to be understood that by incorporating by reference the foregoing and following patents to describe examples of specific members of the novel class with greater particularlity, it is intended that identification of the therein disclosed porous crystalline silicates be resolved on the basis of their respective X-ray diffraction patterns. As discussed above, the present invention contemplates utilization of such catalysts wherein the mole ratio of silica to alumina is essentially unbounded. The incorporation of the identified patents and patent applications should therefore not be construed as limiting the disclosed crystalline zeolites to those having the specific silica-alumina mole ratios discussed therein, it now being known that such zeolites may contain very low amounts of aluminum and yet, having the same crystal structure as the disclosed materials, may be useful or even preferred in some applications. It is the crystal structure, as identified by the X-ray diffraction "fingerprint", which establishes the identity of the specific crystalline zeolite material. The crystal structure of known zeolites may include gallium, boron, iron and chromium as framework elements, without changing its identification by the X-ray diffraction "fingerprint"; and these gallium, boron, iron and chromium containing silicates and aluminosilicates may be useful, or even preferred, in some applications described herein.

Crystalline ZSM-5 and its preparation are described in U.S. Pat. No. 3,702,886. It has a distinctive X-ray diffraction pattern which identifies it from other known crystalline silicates. A crystalline silicate composition having the structure of ZSM-5 is described in U.S. Pat. No. Re. 29,948, the entire disclosure of which is incorporated herein by reference. U.S. Pat. No. 4,139,600 teaches a method for synthesis of zeolite ZSM-5 from a reaction mixture comprising, as a directing agent, an alkyldiamine. U.S. Pat. No. 4,296,083 claims synthesizing zeolites characterized by a constraint index of 1 to 12 and an alumina/silica mole ratio of not greater than 0.083 from a specified reaction mixture containing an organic nitrogen-containing cation provided by a compound such as tetrapropylammonium bromide, triethylamine, trimethylamine, tripropylamine, ethylenediamine, propanediamine, butanediamine, pentanediamine, hexanediamine, methylamine, ethylamine, propylamine, butylamine, dimethylamine, diethylamine, dipropylamine, benzylamine, aniline, pyridine, piperidine and pyrrolidine.

U.S. Pat. No. 4,151,189 claims a method for synthesizing zeolites ZSM-5, ZSM-12, ZSM-35 and ZSM-38 containing an organic nitrogen cation from a specified reaction mixture containing a primary amine having 2 to 9 carbon atoms as a directing agent. U.S. Pat. No. 4,341,748 shows synthesis of ZSM-5 structure from reaction mixtures comprising ethanol, ZSM-5 seeds, ethanol and seeds, ethanol and ammonimum hydroxide, and ethanol, ammonimum hydroxide and seeds. U.S. Pat. No. 4,100,262 teaches synthesis of ZSM-5 from a reaction mixture comprising a tetraalkylammonium source and a tetraureacobalt (II) complex.

The silicon/aluminum atomic ratio of a given zeolite is often variable. For example, zeolite X can be synthesized with silicon/aluminum atomic ratios of from 1 to 1.5, while that ratio in zeolite Y is from 1.5 to 3. In some zeolites, the upper limit of the silicon/aluminum atomic ratio is unbounded. ZSM-5 is one such example wherein the silicon/aluminum atomic ratio is at least 2.5 and up to infinity. U.S. Pat. No. 3,941,871, reissued as U.S. Pat. No. Re. 29,948, discloses a porous crystalline silicate made from a reaction mixture containing no deliberately added aluminum and exhibiting the X-ray diffraction pattern characteristic of ZSM-5.

The exact chemical make-up of zeolites including ZSM-5 can determine the nature of its activity in a particular catalysis. Thus, the chemical make-up of the zeolite, in terms of its silica/alumina atomic ratio is of practical significance.

The silica precursor used in this method of preparation is formed from a solution of a silica source. Conveniently, the solution is an aqueous solution of a pH ranging from 9 to 12. The source of silica can be any soluble silicate and is preferably sodium silicate.

The silica precursor is preferably formed by its continuous precipitation from the solution phase. Accordingly, precipitation preferably comprises initiating precipitation and maintaining said precipitation.

Alteration of the composition of the solution of silica source is undertaken by introducing a precipitating reagent. In one embodiment, the precipitating reagent is a source of acid. Thus, the precipitating reagent can be an acid solution. The acid of the solution may be any mineral acid, such as $H_2SO_4$, HCl, $HNO_3$, etc. The acid solution can have a pH ranging from essentially 0 to about 6. Thus in one embodiment of the invention, precipitation can be effected by acid neutralization of a basic solution of a silicate.

In one of two alternative methods of preparation, the silica can be precipitated alone in the absence of sources of other zeolitic framework elements. In this embodiment, both the precipitating reagent and the solution of silica source can be free of intentionally added alumina or alumina source. That is, no aluminum is deliberately added to the silica precipitation reaction mixture, in this embodiment; however, aluminum is ubiquitous and the presence of such a material in minor amounts is due to impurities in the precursors of the reactants or impurities extracted from the reaction vessel; thus, when no source of alumina is added in the alternative embodiment, the amount of alumina in the silica precursor precipitate generally will be less than about 0.5 and generally lower than 0.2 weight percent. The foregoing embodiment allows greater flexibility in varying the ratios of zeolite elemental components in the zeolite product realized during the crystallization stage in which the silicate is subjected to zeolite production. However, silicate precipitation can be coprecipitation in the presence of soluble sources of other zeolite framework elements including gallium, indium, boron, iron and chromium. The soluble source of these other zeolitic framework components can be e.g., nitrates. The coprecipitation product would be an amorphous material, e.g., gallo-silicate, boro-silicate, or ferrosilicate. Alternatively, soluble sources of gallium, indium, boron, iron and/or chromium can be added with the precipitated silica precursor to the zeolite crystallization stage.

Continuous precipitation of the amorphous silicate precursor, in accordance with this method of preparation, comprises introducing the solution of silica source and the precipitating reagent to a reaction zone while maintaining a substantially constant molar ratio of silica source to precipitating reagent. In one embodiment, the precipitating reagent and the silica source are introduced simultaneously into the reaction zone.

Continuous precipitation of silica precursor effects two results. Firstly, silica gel formation is at least substantially eliminated and secondly, precipitated silica precursor particle size exceeds that silica particle size at which silica gel formation is possible. The precipitated silica precursor comprises agglomerated solids in the shape of microspheres. Suspensions of these particles exhibit low viscosities at high solids loadings in subsequent processing, including zeolite synthesis, for example, even at solids loading equal to or greater than 20-30% and even at 35% solids. This is in marked contrast to non-controlled neutralization which results in a solid, non-stirrable mass. In accordance with the invention, the particle size of the silica precipitate ranges between 1-500 microns but the average size is 50-100 microns.

Other conditions affecting precipitation include time, pH and temperature. The temperature of the precipitation mixture can range from 80° to 300° F. (about 27° C. to 150° C.). The time of contact of the solution of silica source and the precipitating reagent can range from about 10 minutes to several hours at pH maintained from about 6 to 11. Generally, the silica precursor is processed by isolating it, e.g., by filtration, and removing soluble contaminants therefrom, by washing and/or ion exchange. This stage can be considered a solids consolidation step.

The silica precursor can be crystallized to a crystalline silicate (or crystalline aluminosilicate), having an X-ray diffraction pattern corresponding to a known zeolite, in particular, that of ZSM-5. If the crystallographically crystalline material to be produced is to include alumina, gallium, indium, boron, iron, chromium or mixtures thereof, as for example in the ZSM-5 synthesis, that source can be employed after the silica precursor precipitation. In one embodiment of the invention, the source of alumina is added to the crystallization formulation containing the silica precursor for crystallization to produce ZSM-5. The source of alumina can be any aluminum salt, for example, aluminum sulfate. The amount of the source of alumina etc., will depend on the desired ultimate aluminum content of the zeolite and on the zeolite production method. Generally, the $SiO_2/Al_2O_3$ ratio can range from about 20 to infinity. The silica precursor and alumina source can be admixed together in any order without adverse affects.

The crystallographically crystalline silicate is prepared from a crystallization reaction mixture containing the silica precursor alkali metal and water. In preparing the ZSM-5 utilized in the invention herein, no organic, sometimes referred as a "template" or "directing agent"J, is present in the zeolite crystallization reaction mixture. In addition to amines described above, such organic compounds which may be components of the crystallization reaction mixture contain any element of Group VB such as nitrogen or phosphorus, preferably nitrogen. In addition to amines, preferred compounds are quaternary compounds generally expressed by the general formula:

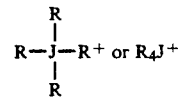

wherein J is an element of Group VB of the Periodic Table, e.g., N or P, preferably N, and each R is an alkyl or aryl group having between 1 and 7 carbon atoms, and preferably at least one R group is a methyl, ethyl, propyl or butyl group. The quaternary compound is generally supplied by introducing into the reaction mixture a composition such as the hydroxide, chloride or bromide of the tetraalkyl derivative of the desired VB element, e.g., tetraethylammonium hydroxide, tetrapropylammonium bromide, tetrapropylammonium hydroxide, tetrabutylphosphonium hydroxide, methyltriethylammonium chloride, and the like. Alkylammonium cation precursors generated in situ by reaction of tertiary amines with alkyl hydroxides or alkyl halide also may be used. The absence of that organic, in accordance with the invention, dictates an $SiO_2:Al_2O_3$ molar ratio of from about 30 to about 100, for ZSM-5 production. By comparison, when ZSM-5 production is undertaken in the presence of such organic, the $SiO_2:Al_2O_3$ ratio can be greater than about 30. The advantage of utilizing this zeolite in the method of the invention, in which no organic is added is reduction in cost and reduction in environmental concerns due to the volatility of certain organics used in the conventional crystallization-synthesis of zeolites. Optionally, the crystallization reaction mixture will contain seeds of suitable zeolite crystals.

Conditions useful in ZSM-5 production in the absence of organics produce the product ZSM-5 of crystal size greater than 0.05 micron. Synthesis conditions, in propylene jars at 100° C. or in stainless steel autoclaves at higher temperatures in the absence of organic and in the absence of seed has produced ZSM-5 of other than small crystals. For the purposes herein, small crystals are defined as having at least one dimension less than about 0.05 micron. In the past, small (having at least one dimension or less than 0.05 micron) crystals formed by methods other than that described herein to produce ZSM-5 have produced spherical crystals (0.03-0.09 micron). Over the total useful range of temperatures of about 80° to about 250° C. for 2-3 hours to 150 days, although ZSM-5 is produced, small crystal ZSM-5 is not produced, in the absence of organic and in the absence of seeds.

Seeding shortens the crystallization time but the resulting crystal size is normally bigger than the seeds. By using about 5% of seeding and with both the silica (i.e. HiSil) and seeds (0.02-0.05 micron) mulled, the resulting crystals were in the range of 0.02-0.1 micron by SEM. The advantage of using over 5% seeding for small crystal formation was not observed.

By lowering the initial reaction temperature to less than about 250° F. (about 121° C.), increasing the solid loadings therein to 20%, preferably greater than 30%, and maintaining a specified level of seeding, ZSM-5 synthesized in the absence of organic has a special thin plate morphology with at least one dimension equal to or less than 0.05 micron and even 0.04 micron in size. By "platelet", is meant that the two dimensions, other than that third dimension of less than about 0.05 micron, substantially form a square.

Preferably, the seeds used are small size (0.02–0.05 micron) ZSM-5 crystals. The percentage of seeding should be about 5–10% if untreated seeds are used. Furthermore, they could be mixed with silica and/or alumina sources to be mulled or attrited (to provide larger surface area and intimate contact among the ingredients) before reaction. Solid loadings of the synthesis mixture should be as high as practical.

Ion exchange of the crystalline silicate materials utilized in the alkylation of aromatics by the present invention can be conducted to effect ammonium exchange at acidic sites of said materials. The source of the ammonium ion is not critical; thus the source can be ammonium hydroxide or an ammonium salt such as ammonium nitrate, ammonium sulfate, ammonium chloride and mixtures thereof. These reagents are usually in aqueous solutions; by way of illustration, aqueous solutions of 1N $NH_4OH$, 1N $NH_4NO_3$, 1N $NH_4Cl$ and 1N $NH_4Cl/NH_4OH$ have been used to effect ammonium ion exchange on these, and similar materials. The pH of the ion exchange is not critical but generally maintained at 7 to 12. Ammonium exchange may be conducted for a period of time ranging from about 0.5 to about 20 hours at a temperature ranging from ambient up to about 100° C. The ion exchange may be conducted in multiple stages. Calcination of the ammonium exchanged will produce the crystalline silicate or zeolite in its acid form. Calcination can be effected at temperatures up to about 600° C.

The crystals of zeolite in a form substantially free of alkali metal, i.e., containing less than about 0.5 weight percent alkali metal, and characterized by an alpha value hereinafter described may then be subjected to thermal treatment, preferably in the presence of steam, to reduce the activity thereof, as expressed in terms of alpha value, as described herein, to less than about 100 and preferably less than about 75, say, between about 30 and about 65. Alternately, such treatment may be accomplished after the zeolite has been composited with inorganic oxide.

The alpha value reflects the relative activity of the catalyst with respect to a high activity silica-alumina cracking catalyst. To determine the alpha value as such term is used herein, n-hexane conversion is determined at about 800° F. Conversion is varied by variation in space velocity such that a conversion level of 10 to 60 percent of n-hexane is obtained and converted to a rate constant per unit volume of zeolite and compared with that of silica-alumina catalyst which is normalized to a reference activity of 1000° F. Catalytic activity of the catalysts are expressed as a multiple of this standard, i.e., the silica-alumina standard. The silica-alumina reference catalyst contains about 10 weight percent $Al_2O_3$ and the remainder $SiO_2$. This method of determining alpha, modified as described above, is more fully described in the Journal of Catalysis, Vol. VI, pages 278–287, 1966.

Thermal treatment will depend on the nature of the atmosphere to which the zeolite is exposed. When such atmosphere is an inert gas, the minimum effective temperature will be about 1200° F. and may extend up to 1800° F. When the treating atmosphere is steam, lower temperatures may be used extending from about 500° F. to about 1800° F. depending on the steam pressure, with the use of higher pressure requiring a lower temperature. This treatment is carried on for a period of time sufficient to effect the desired reduction in alpha. Generally, such period will be between about ½ hour and 100 hours. Such thermal treatment can be carried out in any inert atmosphere such as air, nitrogen, carbon dioxide, carbon monoxide, hydrogen, flue gas, argon, methane, helium, oxygen and suitable mixtures thereof, but is preferably effected in an atmosphere containing steam. A steam treating atmosphere may be employed which is 100 percent steam or steam admixed with a gas which is substantially inert with respect to the zeolite. It is contemplated that the thermal treatment will generally be effected at atmospheric pressure but pressures ranging from sub-atmospheric to several hundred atmospheres may be employed. With the use of elevated pressure, temperatures in the lower region of the above-specified range will usually be applicable in achieving the desired reduction in alpha value of the zeolite under treatment. Thus, it has been found, that at elevated steam pressure, the temperature of treatment can be reduced substantially to achieve the same degree of modification.

In the case of many catalysts, it is desired to incorporate the zeolite ZSM-5 hereby prepared with another material resistant to the temperatures and other conditions employed in certain organic conversion processes. Such matrix materials include active and inactive materials and synthetic or naturally occurring zeolites as well as inorganic materials such as clays, silica and/or metal oxides, e.g. alumina. The latter may be either naturally occurring or in the form of gelatinous precipitates, sols or gels including mixtures of silica and metal oxides. Use of a material in conjunction with the zeolite ZSM-5, i.e. combined therewith, which is active, may enhance the conversion and/or selectivity of the catalyst in certain organic conversion processes. Inactive materials suitably serve as diluents to control the amount of conversion in a given process so that products can be obtained economically without employing other means for controlling the rate or reaction. Frequently, crystalline silicate materials have been incorporated into naturally occurring clays, e.g. bentonite and kaolin. These materials, i.e. clays, oxides, etc., function, in part, as binders for the catalyst. It is desirable to provide a catalyst having good physical strength, because in petroleum refinery processing, the catalyst is often subjected to conditions, which tend to break the catalyst down into powder-like materials which cause problems in processing. Preferably, the porous crystalline silicate is combined in an amount between about 1 and about 99 weight percent in an inorganic oxide binder, e.g., alumina, preferably between about 50 and about 75 weight percent.

Naturally occurring clays which can be composited with the hereby synthesized zeolite ZSM-5 include the montmorillonite and kaolin families which include the sub bentonites, and the kaolins commonly known as Dixie, McNamee, Georgia and Florida clays, or others in which the main mineral constituent is halloysite, kaolinite, dickite, nacrite or anauxite. Such clays, can be used in the raw state as originally mined or initially subjected to calcination, acid treatment or chemical modification.

In addition to the foregoing materials, the zeolite ZSM-5 catalyst used herein can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silicaalumina-magnesia and silica-magnesia-zirconia. The matrix can be in the form of a cogel. A mixture of these components could also be used.

The relative proportions of finely divided crystalline silicate and inorganic oxide gel matrix vary widely with the crystalline silicate content ranging from about 0.1 to about 90 percent by weight, and more usually in the range of about 10 to about 70 percent by weight of the composite.

U.S. application Ser. No. 014,147, cited above, teaches the use of zeolites prepared from a non-organic forming mixture containing precipitated silica of greater than 1 micron in diameter in treating organic compounds such as, for example, those selected from the group consisting of hydrocarbons, alcohols and ethers, for conversion to conversion products such as, for example, aromatics and lower molecular weight hydrocarbons, over a catalytically active form of ZSM-5 by contact under organic compound conversion conditions including a temperature of from about 100° C. to about 800° C. a pressure of from about 0.1 atmosphere (bar) to about 200 atmospheres, a weight hourly space velocity of from about 0.08 $hr^{-1}$ to about 2000 $hr^{-1}$ and a hydrogen-feedstock organic compound mole ratio of from 0 (no added hydrogen) to about 100.

Such conversion processes include alkylating aromatic hydrocarbons, e.g. benzene and alkylbenzenes, in the presence of an alkylating agent, e.g. olefins, formaldehyde, alkyl halides and alcohols, with reaction conditions including a temperature of from about 340° C. to about 500° C., a pressure of from about atmospheric to about 200 atmospheres, a weight hourly space velocity of from about 2 to about 2000 and an aromatic hydrocarbon/alkylating agent mole ratio of from about 1/1 to about 20/1. However, no teaching of improved results by modifying diffusion rate constants and alpha activity is given for such alkylation processes.

Exemplary of the hydrocarbons which may be alkylated by the process of the present invention are aromatic compounds such as benzenes, naphthalenes, anthracenes, and the like and substituted derivatives thereof; and alkyl substituted aromatics, e.g. toluene, xylene and homologs thereof.

In accordance with this invention the alkylating agents employed are olefinic hydrocarbons having from 2 to 20 carbon atoms such as ethylene, propylene, and dodecylene, preferably having from 2 to 10 carbon atoms.

Operating conditions employed in the process of the present invention will be dependent, at least in part, on the specific alkylation reaction being effected. Such conditions as temperature, pressure, space velocity and molar ratio of the reactants and the presence of inert diluents will have important effects on the process. Accordingly, the manner in which these conditions affect not only the conversion and distribution of the resulting alkylated products but also the rate of deactivation of the catalyst will be described below.

The process of this invention can be conducted such that alkylation of an aromatic hydrocarbon compound, exemplified by benzene, is carried out by contact in a reaction zone, such as, for example, a fixed bed of catalyst, under alkylation effective conditions, said catalyst being characterized as above-described and preferably hydrogen exchanged such that a predominate portion of its exchangeable cations are hydrogen ions. In general, it is contemplated that more than 50 percent and preferably more than 75 percent of the cationic sites of the crystalline zeolite, above-described, will be occupied by hydrogen ions. The alkylatable aromatic compound and olefinic hydrocarbon, e.g., ethylene are desirably fed to a first stage at an appropriate mole ratio of one to the other. The feed to such first stage is heated. After some reaction takes place, such as, for example, when about 80% of the olefinic hydrocarbon is consumed, the effluent of the first stage is cooled to remove heat of reaction and more olefinic hydrocarbon is added (second stage) to maintain the mole ratio of aromatic compound to olefinic hydrocarbon within the range established for the first stage. A plurality of reaction stages are possible for the process of this invention. It is generally desirable to provide cooling between reactor stages.

Considering vapor-phase alkylation of benzene with ethylene, the first stage mole ratio of benzene to ethylene may be in the range of about 1:1 to about 30:1. The first stage feed is heated to a reactor inlet temperature within the range of about 575° F. to about 900° F. at a pressure within the range of about atmospheric to about 3000 psig. Preferred inlet temperatures fall within the range of about 600° F. to about 850° F. and preferred pressures fall within the range of about 25 psig to about 450 psig. The repeating of reaction staging is carried out while maintaining an overall aromatic hydrocarbon, e.g., benzene, to alkylating agent, e.g. ethylene, mole ratio of about 1:1 to about 30:1, with a preferred range of about 2.5:1 to about 25:1.

It is noted that extremely high total feed space velocities are possible in the process of this invention, i.e. up to 2000 lb. total feed/hr.-lb. crystalline silicate composition. An important factor in the present process is, however, the weight hourly space velocity (WHSV) of the alkylating agent, e.g. ethylene. The alkylating agent WHSV to each of any alkylation reactor stages is maintained between about 1 and about 10 lb. alkylating agent/hr.-lb. crystalline aluminosilicate. For the most desirable alkylating agent, i.e., ethylene, WHSV is within the range of about 2 to about 8 lb. ethylene/hr.-lb. crystalline aluminosilicate. When the ethylene WHSV is maintained within the above limits, an economical cycle between regeneration of catalyst exists.

The process of this invention may be carried out as a batch-type, semi-continuous or continuous operation utilizing a fixed or moving bed catalyst system. A preferred embodiment entails use of a fluidized catalyst zone wherein the reactants, e.g. benzene and ethylene, are passed concurrently or countercurrently through a moving fluidized bed of the catalyst. The fluidized catalyst after use is conducted to a regeneration zone wherein coke is burned from the catalyst in an oxygen-containing atmosphere, e.g. air, at an elevated temperature, after which the regenerated catalyst is recycled to the conversion zone for further contact with the benzene and ethylene reactants.

In another aspect, the present invention relates to a method for effecting alkylation of an aromatic hydrocarbon charge whereby o-xylene production is minimized which comprises contacting said aromatic hydrocarbon charge with an olefinic hydrocarbon alkylating agent under conditions effective for accomplishing said alkylation in the presence of a catalyst composition having an alpha value below about 100. The catalyst composition comprises a porous crystalline silicate whose crystals have a diffusion rate constant of at least about 100 $sec^{-1}$.

The porous crystalline silicate employed can be aluminosilicate having a silica to alumina molar ratio of less than about 40, preferably between about 20 and about 30. The alpha value of the catalyst composition can be adjusted to below about 100, preferably below about 75, say from about 30 to about 65, by steaming at a temperature of about 500° F. to about 1800° F., preferably between about 750° and about 1200° F. Preferably, the alkylation process of the present invention is effected in the vapor phase, said aromatic hydrocarbon is benzene and said olefinic hydrocarbon alkylating agent is ethylene.

BRIEF DESCRIPTION OF THE DRAWING

The drawing is a schematic representation of the apparatus and processing steps used in preparing the catalyst used in the present invention.

EMBODIMENTS

Preparation of the porous crystalline silicate used in the present invention will now be described with reference to the FIGURE of the drawing. A dilute solution of sulfuric acid or a mixture of dilute sulfuric acid and dilute aluminum sulfate, i.e. acid alum solution, is passed via line 1, and a dilute aqueous solution of sodium silicate is passed via line 2 to continuous reactor 3 under sufficient conditions to produce a precipitate-containing reaction product thereof. The contents of reactor 3 are preferably stirred sufficiently to form a visible vortex. Flow rates are controlled to yield an apparent residence time in reactor 3 of about 30 minutes, for example, although residence times greater than about 3 minutes are suitable. Solution strengths are such that the solids content of the resulting slurry ranges from about 5 wt. % to about 20 wt. %, preferably about 10 to 15 wt. %.

The reaction product from reactor 3 is passed via line 4 to a first filtering means 5, e.g. a belt filter, whereupon it is washed with water from line 6. The washed material from first filtering means 5 is passed via line 7 to charge tank 8, along with water from line 9, sodium hydroxide solution, if desired, from line 10, and, if desired, an aqueous slurry containing seed crystals of ZSM-5, from line 11. If aluminum sulfate was not included in the line 1 feed to continuous reactor 3, e.g. as an acid alum solution, then it may be added, if desired, to the charge tank 8 at this time via line 12 as an aqueous solution of, for example, about 47 wt. %. The contents of charge tank 8 are preferably stirred sufficiently to maintain suspension of solids.

The resulting mixture from charge tank 8 is charged batch-wise or continuously via line 13 to crystallizer 14. Crystallizer 14 is brought to and maintained at conditions sufficient for crystals of ZSM-5 to form, including a temperature of from about 90° C. to about 250° C., a residence time of from about 3 hours to about 100 hours and with stirring to provide adequate heat transfer and suspension of solids.

The reaction mixture in crystallizer 14 will have a composition in mole ratios within the ranges of

| | |
|---|---|
| $SiO_2/Al_2O_3 =$ | greater than about 20 |
| $H_2O/SiO_2 =$ | 1 to 200 |
| $OH^-/SiO_2 =$ | 0.02 to 0.4 |
| $(M_{2/n}O)/SiO_2 =$ | 0.02 to 0.30. | where M is an alkali metal or alkaline earth metal and n is the valence of M.

Slurry containing product crystals of ZSM-5 structure is removed from crystallizer 14 via line 23 and passed into surge tank 24 with sufficient stirring to maintain suspension. For purposes of seeding further batches, if desired, a first part of the surge tank 24 slurry, e.g., from 0 wt. % to about 10 wt. %, is passed via line 25 to a slurry device 26 optionally comprising a particle size reduction means, such as, for example, a ball mill, to maximize surface area of such particles.

Slurry having undergone contact with the particle size reduction means of the slurry device 26 may be passed via line 11 to charge tank 8 as needed.

A second part of the surge tank 24 slurry, e.g., from about 90 wt. % to about 100 wt. %, is passed via line 27 to a second filtering means 28, e.g., a belt filter, whereupon it is washed with water, first, from line 29, and optionally with dilute solution of ammonium salt, e.g. nitrate, second, from line 30, sufficient to effect ion-exchange of the ZSM-5. The washed material from the second filtering means 28 is passed via line 31 to, for instance, dryer 32 operated at a temperature of from about 100° C. to about 300° C. Recovered from dryer 32 via line 33 is a ZSM-5 product useful in the present invention.

The flow rates in the lines of the drawing can be adjusted to be operated in a semi-batchwise or continuous fashion.

The zeolite ZSM-5 composition as prepared hereby can be identified, in terms of mole ratios of oxides and in the anhydrous state, as follows:

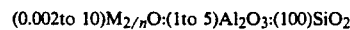

$(0.002 \text{ to } 10)M_{2/n}O:(1 \text{ to } 5)Al_2O_3:(100)SiO_2$ wherein M is at least one cation having a valence n.

The original cation can be replaced, at least in part, by ion exchange with another cation. Thus, the original cations are exchanged into a hydrogen form or a form in which the original cation has been replaced by a metal of Groups IIA, IIIA, IVA, IB, IIB, IIIB, IVB, VIB or VIII of the Periodic Table. Catalytically active forms of these would include, in particular, hydrogen, rare earth metals, aluminum, metals of Groups II and VIII of the Periodic Table and manganese.

The X-ray diffraction pattern of the crystalline silicate product of the present invention has the characteristic lines shown in Table 1.

TABLE 1

| interplanar d-Spacing (A) | Relative Intensity ($I/I_o$) |
|---|---|
| 11.1 ± 0.3 | s |
| 10.0 ± 0.3 | s |
| 7.4 ± 0.2 | w |
| 7.1 ± 0.2 | w |
| 6.3 ± 0.2 | w |
| 6.04 ± 0.2 | w |
| 5.56 ± 0.1 | w |
| 5.01 ± 0.1 | w |
| 4.60 ± 0.08 | w |
| 4.25 ± 0.08 | w |
| 3.85 ± 0.07 | vs |
| 3.71 ± 0.05 | s |
| 3.04 ± 0.03 | w |
| 2.99 ± 0.02 | w |
| 2.94 ± 0.02 | w |

These values were determined by standard technique. The radiation was the K-alpha doublet of copper, and a diffraction equipped with a scintillation counter and a strip chart pen recorder was used. The peak heights, I, and the positions as a function of two times theta, where theta is the Bragg angle, were read from the spectrometer chart. From these, the relative intensities, 100 $I/I_o$ where $I_o$ is the intensity of the strongest line or peak, and d (obs.), the interplanar spacing in Angstrom units (A) corresponding to the recorded lines, were calculated. In Table 1 the relative intensities are given in terms of the symbols w=weak, s=strong, and vs=very strong. Ion exchange of the sodium ions with cations reveals substantially the same pattern with some minor shifts in interplanar spacing and variation in relative intensity. Other minor variations can occur depending on the silicon to aluminum ratio of the particular sample, as well as if it has been subjected to thermal treatment.

Synthetic zeolite ZSM-5 prepared in accordance herewith can be used in the alkali metal form, hydrogen form or another univalent or multivalent cationic form. It can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such components can be exchanged into the composition, impregnated therein or physically intimately admixed therewith. Such components can be impregnated in or on zeolite ZSM-5 such as, for example, by, in the case of platinum, treating the zeolite with a platinum metal-containing ion. Suitable platinum compounds for this purpose include chloroplatinic acid, platinous chloride and various compounds containing the platinum amine complex. Combinations of metals and methods for their introduction can also be used.

Synthetic zeolite ZSM-5, when employed either as an adsorbent or as a catalyst in a hydrocarbon conversion process, should be dehydrated at least partially. This can be done by heating to a temperature in the range of from about 200° C. to about 600° C. in an inert atmosphere, such as air, nitrogen, etc. and at atmospheric or subatmospheric pressures for between about 1 and 48 hours. Dehydration can also be performed at lower temperature merely by placing the zeolite in a vacuum, but a longer time is required to obtain a particular degree of dehydration. The thermal decomposition product of the newly synthesized ZSM-5 can be prepared by heating same at a temperature up to about 550° C. for from about 1 hour to about 48 hours.

As above mentioned, synthetic zeolite ZSM-5 prepared in accordance herewith can have the original cations associated therewith replaced by a wide variety of other cations according to techniques well known in the art. Typical further replacing cations include metal cations and mixtures thereof. Of the replacing metallic cations, particular preference is given to cations of metals such as rare earths, Ga, Mn, Ca, Mg, Zn, Cd, Pd, Ni, Cu, Ti, Al, Sn, Fe and Co.

Typical ion exchange technique would be to contact the synthetic zeolite with an aqueous solution of a salt of the desired replacing cation or cations. Although a wide variety of salts can be employed, particular preference is given to chlorides, nitrates and sulfates.

Representative ion exchange techniques are disclosed in a wide variety of patents including U.S. Pat. Nos. 3,140,249; 3,140,251; and 3,140,253.

Following contact with the metal salt solution of the desired replacing cation, the zeolite is then preferably washed with water and dried at a temperature ranging from 65° C. to about 315° C. and thereafter may be calcined in air or an inert gas at temperatures ranging from about 200° C. to about 550° C. for periods of time ranging from about 1 to about 48 hours or more to produce a catalytically-active thermal decomposition product thereof.

The following examples will serve to illustrate the process of the invention without limiting the same.

EXAMPLE 1

Preparation of Small Crystal ZSM-5 From Forming Mixture Containing Organic

A 3.1 parts quantity, by weight, of n-propylamine was added to a mixture containing 1.1 parts sodium chloride, 0.2 parts ZSM-5 seeds, 0.2 parts dispersant (mixture of polymerized aryl and substituted benzoid alkyl sulfonic acids), 2.6 parts $Al_2(SO_4)_3.14\ H_2O$, 7.0 parts 50% NaOH, 25.8 parts amorphous precipitated silica (HiSil 233) and 59.9 parts water. The reaction mixture had a composition, in mole ratios, of:

| | |
|---|---|
| $SiO_2/Al_2O_3 =$ | 65 |
| $H_2O/SiO_2 =$ | 9.92 |
| $OH^-/SiO_2 =$ | 0.163 |
| $N/Al_2O_3 =$ | 9.2 |
| $OH^-/H_2O =$ | 0.0165 | wherein N is the n-propylamine. The hydroxide concentration is based on only inorganic sources.

The reaction mixture was then heated directly to 220° F. and stirred in an autoclave at that temperature for crystallization. After full crystallinity was achieved, the resulting crystals were separated from the remaining liquid by filtration, washed with water, exchanged with $NH_4NO_3$ and dried.

The resulting product had a $SiO_2/Al_2O_3$ molar ratio of about 50, a diffusion rate constant $(D/r^2)$ of greater than 150 $sec^{-1} \times 10^{-6}$ and was composited with alumina binder to form a material having a ZSM-5 content of about 65 weight percent and an alpha of about 200. After steaming in 100% steam for 3 hours the alpha value was measured at about 40.

EXAMPLE 2

Preparation of Small Crystal ZSM-5 from Non-Organic, Seeded Forming Mixture

A 7.3 parts quantity, by weight, of water was mixed with 12.8 parts 50% NaOH, 10.1 parts $Al_2(SO_4)_3.14-H_2O$, 1.6 parts ZSM-5 seeds and 68.2 parts amorphous silica (47.6% solids) prepared by the neutralization of sodium silicate with sulfuric acid. The reaction mixture had a composition, in mole ratios, of:

| | |
|---|---|
| $SiO_2/Al_2O_3 =$ | 32 |
| $H_2O/SiO_2 =$ | 5.45 |
| $OH^-/SiO_2 =$ | 0.105 |
| $OH^-/H_2O =$ | 0.0192 |

The reaction mixture was then heated directly to 220° F. and stirred in an autoclave at that temperature for crystallization. After full crystallinity was achieved, the resulting crystals were separated from remaining liquid by filtration, washed with water and dried.

The resulting product has a $SiO_2/Al_2O_3$ molar ratio of about 25, a diffusion rate constant $(D/r^2)$ greater than about 200 $sec^{-1} \times 10^{-6}$ and was composited with alumina binder so that the resulting product had a ZSM-5 content of about 65 weight percent and an alpha value of about 500.

After 8 hours of steaming in 100% steam at 1000° F., the alpha value was reduced to about 40.

EXAMPLE 3

Ethylation of Benzene Using ZSM-5

The catalysts of Examples 1 and 2 were evaluated in a fixed bed reactor for the ethylbenzene reaction. The result is shown in Table 2. It is clear that under similar conditions and ethylene conversion, the by-product formation was similar for the two catalysts except the o-xylene selectivity. The yield of o-xylene from Example 2 was reduced by half.

TABLE 2

| Feed: | Benzene, 380 cc/hr: Ethylene, 160 cc/min | |
|---|---|---|
| Temperature: | 750° F. | |
| WHSV: | 4 (based on ethylene) | |
| Pressure: | 300 psig | |
| Catalyst | Example No. 1 | Example No. 2 |
| Ethylene Conversion | 98% | 98% |
| DIEB/EB | 0.082 | 0.086 |
| O-Xyl/EB X$10^{-4}$ | 1.800 | 0.900 |
| Xyl/EB X$10^{-4}$ | 11.600 | 12.900 |
| C$_9$+/EB | 0.086 | 0.098 |

What is claimed is:

1. A method for effecting alkylation of an aromatic hydrocarbon charge which comprises contacting said aromatic hydrocarbon charge with an olefinic hydrocarbon alkylating agent under conditions effective for accomplishing said alkylation in the presence of a catalyst composition having an alpha value below about 100 which comprises ZSM-5 having a SiO$_2$/Al$_2$O$_3$ molar ratio of less than 100 and whose crystals have a thin plate morphology with at least one dimension equal to or less than 0.05 micron and an o-xylene diffusion rate constant measured at 30% of total o-xylene capacity of at least about 100 sec$^{-1}$×$10^{-6}$.

2. The method of claim 1 wherein said conditions include a reactor inlet temperature between about 575° F. and about 900° F., a reactor pressure between atmospheric and about 3000 psig, employing a mole ratio of hydrocarbon aromatic charge to olefinic hydrocarbon alkylating agent in the approximate range of 1:1 to 30:1 and a total weight hourly space velocity between about 2 and about 2000.

3. The method of claim 2 wherein said alkylating agent is an olefinic hydrocarbon containing from 2 to 20 carbon atoms.

4. The method of claim 1 wherein said alpha value is adjusted to within the range of about 30 to about 65.

5. The method of claim 4, wherein alpha value is adjusted by steaming at a temperature of about 500° F. to about 1800° F.

6. The method of claim 1 wherein said composition comprises ZSM-5 in an amount between about 1 and about 99 weight percent and an inorganic oxide binder.

7. The method of claim 6 wherein said binder is alumina.

8. The method of claim 7 wherein said alkylation is effected in the vapor phase, said aromatic hydrocarbon charge comprises benzene and said olefinic hydrocarbon alkylating agent comprises ethylene.

9. The method of claim 8 wherein said reactor inlet temperature is between about 600° F. and about 850° F. and the reactor pressure is between about 25 and about 450 psig.

10. The method of claim 7 wherein said composition comprises ZSM-5 in an amount between about 50 and about 75 weight percent.

11. The method of claim 1, wherein said charge comprises toluene.

12. The method of claim 1 wherein said diffusion rate constant is at least about 150 sec$^{-1}$×$10^{-6}$.

13. The method of claim 1, wherein said conditions include a reactor inlet temperature between about 575° F. and about 1000° F., a reactor pressure between atmospheric and about 3000 psig, employing a mole ratio of hydrocarbon aromatic charge to olefinic hydrocarbon alkylating agent in the approximate range of 1:1 to 30:1 and a total weight hourly space velocity between about 2 and about 2000.

14. In a method for effecting catalytic alkylation with ethylene of an aromatic hydrocarbon charge containing benzene which method exhibits a selectivity for o-xylene production, the improvement which comprises decreasing o-xylene production, by contacting said aromatic hydrocarbon charge with a catalyst composition and an olefinic hydrocarbon alkylating agent under conditions which include a reactor inlet temperature between about 575° F. and about 1000° F., a reactor pressure between atmospheric and about 3000 psig, employing a mole ratio of hydrocarbon aromatic charge to olefinic hydrocarbon alkylating agent in the approximate range of 1:1 to 30:1 and a total weight hourly space velocity between about 2 and about 2000 and said catalyst composition having an alpha value below about 100 which comprises ZSM-5, of crystals having a SiO$_2$/Al$_2$O$_3$ molar ratio of less than 100 and whose crystals have a thin plate morphology with at least one dimension equal to or less than 0.05 micron and an o-xylene diffusion rate constant measured at 30% of total o-xylene capacity of at least about 100 sec$^{-1}$×$10^{-6}$ and recovering ethylbenzene.

15. The method of claim 14, wherein said alpha value is adjusted to within the range of about 30 to about 65.

16. The method of claim 14 wherein said composition comprises ZSM-5 in an amount between about 1 and about 99 weight percent and an inorganic oxide binder.

17. The method of claim 16 wherein said binder is alumina.

18. The method of claim 14 wherein the temperature is between about 600° F. and about 850° F. and the pressure about 25 and about 450 psig.

19. The method of claim 15 wherein said ZSM-5 is present in an amount between about 50 and about 75 weight percent.

20. The method of claim 14 wherein said diffusion rate constant is at least about 150 sec$^{-1}$×$10^{-6}$.

21. The method of claim 14 wherein said ZSM-5 is prepared from a non-gelling, non-organic reaction mixture having a solids content of at least 30 weight percent, comprising a silica source having a particle size of 1 to 500 microns.

22. The method of claim 14, wherein alpha value is adjusted by steaming at temperature of about 500° F. to about 1800° F.

23. The method of claim 14, wherein the ZSM-5 has a framework silica:alumina molar ratio which is less than about 40.

* * * * *